United States Patent
Righettini et al.

(10) Patent No.: US 9,869,620 B2
(45) Date of Patent: Jan. 16, 2018

(54) MEASUREMENT DEVICE FOR MEASURING DYNAMOMETRIC FEATURES OF ELONGATED TEXTILE SAMPLES OF THE YARNS, THREADS, TAPES TYPE AND THE LIKE

(71) Applicant: MESDAN S.p.A., Puegnago del Garda (IT)

(72) Inventors: Paolo Righettini, Toscolano Maderno (IT); Andrea Ginammi, Mapello (IT)

(73) Assignee: MESDAN S.p.A., Puegnago del Garda (IT)

( * ) Notice: Subject to any disclaimer, the term of this patent is extended or adjusted under 35 U.S.C. 154(b) by 0 days.

(21) Appl. No.: 15/295,175

(22) Filed: Oct. 17, 2016

(65) Prior Publication Data

US 2017/0108416 A1 Apr. 20, 2017

(30) Foreign Application Priority Data

Oct. 20, 2015 (IT) .................. 102015000063310

(51) Int. Cl.
*G01N 3/08* (2006.01)
*G01N 3/02* (2006.01)
(Continued)

(52) U.S. Cl.
CPC .............. *G01N 3/08* (2013.01); *G01L 5/008* (2013.01); *G01L 5/009* (2013.01); *G01L 5/04* (2013.01);
(Continued)

(58) Field of Classification Search
CPC .. G01N 3/08; G01N 3/02; G01N 3/04; G01N 3/26; G01N 33/36; G01N 33/265; G01L 5/008; G01L 5/009; G01L 5/04
(Continued)

(56) References Cited

U.S. PATENT DOCUMENTS 4,825,702 A * 5/1989 Cizek .................. G01N 3/08
73/828
5,050,437 A * 9/1991 Etter .................. G01N 3/08
73/830

(Continued)

FOREIGN PATENT DOCUMENTS

GB 326710 3/1930

OTHER PUBLICATIONS

Italian Search Report issued Jul. 4, 2016 in Italian Application UB20154807 filed on Oct. 20, 2015 ( with English translation of Categories of Cited Documents).

*Primary Examiner* — Jewel V Thompson (74) *Attorney, Agent, or Firm* — Oblon, McClelland, Maier & Neustadt, L.L.P.

(57) ABSTRACT

A measurement device for measuring dynamometric features of elongated textile samples of the yarns, threads, tapes type and the like, such a device comprises a first clamp and a second clamp that is substantially aligned and relatively movable with respect to the first clamp along a first translation direction, each of the first clamp and the second clamp including a fixed jaw and a movable jaw in relation to the respective fixed jaw along a second translation direction substantially orthogonal to the first translation direction and the movable jaw is movable between a resting position and an operating position.

17 Claims, 9 Drawing Sheets

(51) Int. Cl.
   *G01N 33/36*   (2006.01)
   *G01N 3/04*   (2006.01)
   *G01N 3/26*   (2006.01)
   *G01L 5/00*   (2006.01)
   *G01L 5/04*   (2006.01)

(52) U.S. Cl.
   CPC ............. *G01N 3/02* (2013.01); *G01N 3/04* (2013.01); *G01N 3/26* (2013.01); *G01N 33/36* (2013.01); *G01N 33/365* (2013.01)

(58) Field of Classification Search
   USPC ............. 73/827, 828–831, 160, 860, 9
   See application file for complete search history.

(56) References Cited

U.S. PATENT DOCUMENTS

| | | | | |
|---|---|---|---|---|
| 5,299,462 | A * | 4/1994 | Key | G01L 5/0047 473/556 |
| 5,329,820 | A * | 7/1994 | McMahon | G01N 3/04 73/833 |
| 5,351,535 | A * | 10/1994 | Etter | G01N 3/08 226/92 |
| 6,318,166 | B1 * | 11/2001 | Roos | G01N 3/08 73/160 |
| 7,810,397 | B2 * | 10/2010 | Aseere | G01N 3/08 73/760 |
| 2013/0180313 | A1 | 7/2013 | Nowrouzieh et al. | |

\* cited by examiner

MEASUREMENT DEVICE FOR MEASURING DYNAMOMETRIC FEATURES OF ELONGATED TEXTILE SAMPLES OF THE YARNS, THREADS, TAPES TYPE AND THE LIKE

The present invention refers to a measurement device for measuring dynamometric features of elongated textile samples of the yarns, threads, tapes, roves type and the like.

The quality control of a yarn is of fundamental importance to control both the production processes and the subsequent treatment processes thereof.

Quality controls are aimed at determining various structural or physical-mechanical features of the yarns including, in particular, the dynamometric features such as the elongation at break by tension, the tensile strength (i.e. the maximum stress under tension before breaking), the elastic modulus under tension and the relative stress/strain curve.

For this purpose, automatic devices for carrying out dynamometric tests have been known for a long time, which generally consist of a pair of clamps that are arranged vertically on top of one another and the upper clamp of which is fixed and the lower clamp is movable in translation towards and away from the fixed clamp.

The fixed clamp is connected to detection means for detecting the tensile force that is applied to the textile sample being tested by means of the movable clamp, said detection means generally consisting of a loading cell. In known devices the fixed clamp is rigidly connected to the loading cell. In them, moreover, the movable clamp is driven to slide with respect to the fixed clamp by means of a recirculating balls screw-nut screw (screw-volute) coupling. In particular, the movable clamp is fixed onto a carriage that is slidably mounted along a rectilinear guide parallel to the sliding direction with respect to the fixed clamp. This carriage is fixed to a nut screw in which a screw couples parallel to the sliding direction of the movable clamp with respect to the fixed clamp and set in rotation by an electric motor by means of transmission means, for example of the belt type. The position of the movable clamp is detected indirectly from the pitch of the screw and the number of revolutions of the motor. In known devices, moreover, each of the two clamps comprises a fixed jaw and a movable jaw towards and away from the respective fixed jaw for clamping and releasing a corresponding portion of the textile sample being tested.

These devices of the known type have some drawbacks.

A first drawback consists of the fact that the clamping surfaces of the jaws of each clamp, whether they are made of steel or are provided with inserts made of elastomeric material, due to wearing and/or deformations, are unable to stably and securely clamp the corresponding portion of the textile sample, thus making it possible for slidings of the latter to occur, which can cause measurement errors. If, then, the clamping surfaces and, in particular, the clamping surface of the movable jaw is made of a membrane of elastomeric material, it must be of large size to ensure adequate clamping forces, which, therefore, translates into considerable/large total bulks.

A second drawback consists of the fact that the rigid coupling of the fixed clamp with the loading cell introduces hyperstaticity in the system and constitutes a pre-load of the cell itself that have a negative impact on the force measurements. While each test is being carried out, moreover, the path followed by the sample being tested could undergo unpredictable deviations with respect to the vertical, such deviations generating undesired force components that anyway are detected by the loading cell.

Yet another drawback consists of the fact that the screw-nut screw movement of the movable clamp with respect to the fixed clamp requires the use of expensive mechanical components and allows obtaining the position of the movable clamp just indirectly. The purpose of the present invention is to avoid the drawbacks of the prior art.

In this general purpose, a particular purpose of the present invention is to provide a measurement device for measuring dynamometric features of elongated textile samples of the yarns, threads, tapes, roves type and the like that allows to stably and securely clamp the textile sample being tested, avoiding undesired slidings thereof and independently from the position of the textile sample with respect to the jaws of the clamps.

Another purpose of the present invention is to provide a measurement device for measuring dynamometric features of elongated textile samples of the yarns, threads, tapes, roves type and the like that allows obtaining more precise and accurate force measurements and independent from the more or less centered position of the textile sample with respect to the jaws of the clamps.

Yet another purpose of the present invention is to provide a measurement device for measuring dynamometric features of elongated textile samples of the yarns, threads, tapes, roves type and the like that allows moving the movable clamp with respect to the fixed one and to detect the position thereof in a simple and precise manner.

Yet another purpose of the present invention is to provide a measurement device for measuring dynamometric features of elongated textile samples of the yarns, threads, tapes, roves type and the like that is structurally simple, functional and cost effective.

These and other purposes are accomplished by a measurement device for measuring dynamometric features of elongated textile samples of the yarns, threads, tapes, roves type and the like as defined in claim 1.

Further features are defined in the dependent claims.

The features and advantages of a measurement device for measuring dynamometric features of elongated textile samples of the yarns, threads, tapes, roves type and the like according to the present invention will become clearer from the following description, given as an example and not for limiting purposes, referring to the attached schematic drawings, in which.

With particular reference to the attached figures, a measurement device for measuring dynamometric features of elongated textile samples of the yarns, threads, tapes, roves type and the like has been wholly indicated with 10.

In the following description reference will be made to the device 10 in its usual position of use referring to a Cartesian system XYZ in which the plane XY indicates a horizontal plane or in any case parallel to the ground on which the device 10 rests and the axis Z is the vertical axis, in which the plane ZY is parallel to the directions along which the relative translation movements between the two clamps and the jaws of each clamp take place as described hereinafter.

The device 10 comprises a housing 11 that can rest on the ground and containing the structural and functional modules necessary for the operation thereof and that are not illustrated and described in detail except for what is relevant for understanding the present invention.

The device 10 comprises a first clamp 12 and a second clamp 13 that are accessible from the front face of the housing 11 (parallel to the plane ZY). The second clamp 13 is aligned to the first clamp 12 and is made movable in relation to it along a first translation direction A. In other words, the second clamp 13 is made movable with rectilinear movement along the first translation direction A towards and away from the first clamp 12 by means of movement means described hereinafter with reference to FIGS. 13 and 14.

Considering the device 10 in its usual use configuration, the first translation direction A is vertical (parallel to the axis Z) and the first clamp 12 is arranged above (i.e. at a greater height with respect to the horizontal plane XY) with respect to the second clamp 13. The first clamp 12 is fixed with respect to the second clamp 13; namely, the first clamp 12 does not carry out translation movements along the first translation direction A with respect to the second clamp 13.

The first clamp 12 and the second clamp 13 each comprise a fixed jaw and a movable jaw in relation to the respective fixed jaw along a second translation direction B substantially orthogonal to the first translation direction A. The movable jaw is movable between a resting position, in which it is spaced apart with respect to the respective fixed jaw, and a working position, in which it is near to the respective fixed jaw for clamping a respective portion of an elongated textile sample, not shown in the attached figures, against it.

The fixed jaw and the movable jaw of the first clamp 12 and of the second clamp 13 are respectively indicated with reference numerals 14 and 15 and with 16 and 17.

The first clamp 12 is then coupled with first detection means 47 adapted to detect the tensile force applied to the textile sample being tested by means of the second clamp 13. Second detection means 48 are also provided for detecting the movement of the second clamp 13 with respect to the first clamp 12 as described hereinafter with reference to FIGS. 13 and 14.

According to a first aspect of the present invention at least one of the fixed jaw 14, 16 and the movable jaw 15, 17 of at least one of the first clamp 12 and the second clamp 13 comprises a base body to which a clamping body is coupled, said clamping body being provided with a clamping surface that faces a corresponding surface of the other respective jaw for clamping the respective portion of textile sample against it, wherein the clamping body is coupled to the base body so as to be able to carry out oscillations with respect to at least two oscillation axes that are different from each other and, advantageously, orthogonal. In particular, the clamping body is coupled to the base body by means of a spherical joint.

In the embodiment represented in the attached figures, the movable jaw 15, 17 of both the first clamp 12 and the second clamp 13 has a structure like the one indicated above. Hereinafter, therefore, the structure of just the first clamp 12 is described in detail, the structure of the second clamp 13, limited to this first aspect of the present invention (i.e. the sole configuration of the two fixed and movable jaws), being totally analogous.

The fixed jaw 14 and the movable jaw 15 each comprise a respective base body 18, 19 that is fixed, for example by means of screws 20, to a support plate 21 that, apart from oscillations made possible by releases as described hereinafter, is generally parallel to the plane ZY.

The base body 18, 19 does not necessarily consist of a unique body, instead it can consist, for assembly needs, of more elements constrained to one another.

The base body 18 of the fixed jaw 14 is fixed to the respective clamping body 22, which has a clamping surface 22a facing the movable jaw 15. The clamping body 22 is rigidly constrained, both in translation and in rotation, to the base body 18, for example by means of the threaded stem of a screw 23 that is inserted into a through-hole 24 obtained in the base body 18 and engages in a blind threaded hole 25 obtained in the clamping body 22 and accessible from the surface thereof opposite the clamping surface 22a.

The base body 19 of the movable jaw 15 is coupled to the respective clamping body 26 that has a clamping surface 26a facing the clamping surface 22a of the clamping body 22 of the fixed jaw 14.

The clamping body 26 is coupled to the base body 19 so as to be able to carry out oscillations at least with respect to two axes that are different from each other and, advantageously, orthogonal and, advantageously, by means of a spherical joint.

In greater detail, the clamping body 26 must be able to translate along the second translation direction B towards and away from the clamping body 22 of the fixed jaw 14; for this purpose, therefore, a linear actuator 27 is provided, which is coupled to the clamping body 26 for actuating the translation movement in both senses along the second translation direction B.

The clamping body 26 is coupled to the movable element of the linear actuator 27 or to the connection element of the linear actuator 27 by means of a spherical joint 28.

With particular reference to the embodiment shown in the attached figures, the linear actuator 27 is of the double-acting pneumatic cylinder 29 and piston 30 type. The cylinder 29 is defined by a cylindrical seat obtained in the base body 19 and inside which the piston 30 is slidably mounted along the second translation direction B; the compressed air is fed in the cylinder 29 by means of fittings 31 supported by the plate 21.

The base body 19 supports in a sliding manner a stem 32 that extends parallel to the second translation direction B; the stem 32 has one end fixed to the piston 30 and the opposite end facing towards the fixed jaw 14 and to which the clamping body 26 is coupled by means of the spherical joint 28.

The clamping body 26 can thus carry out oscillations with respect to at least two axes distinct from one another so that the clamping surface 26a thereof can rest on the clamping surface 22a of the clamping body 22 of the fixed jaw 14 "adapting" and "conforming itself" to it so as to stably clamp the corresponding portion of the textile sample, irrespective of the position of such a sample with respect to the two jaws of the same clamp.

Also in this case it is specified that the clamping bodies 22, 26 do not necessarily consist of a unique body, instead it can consist, in particular for assembly needs, of more elements rigidly constrained to one another.

Figures 6, 7, 7A:
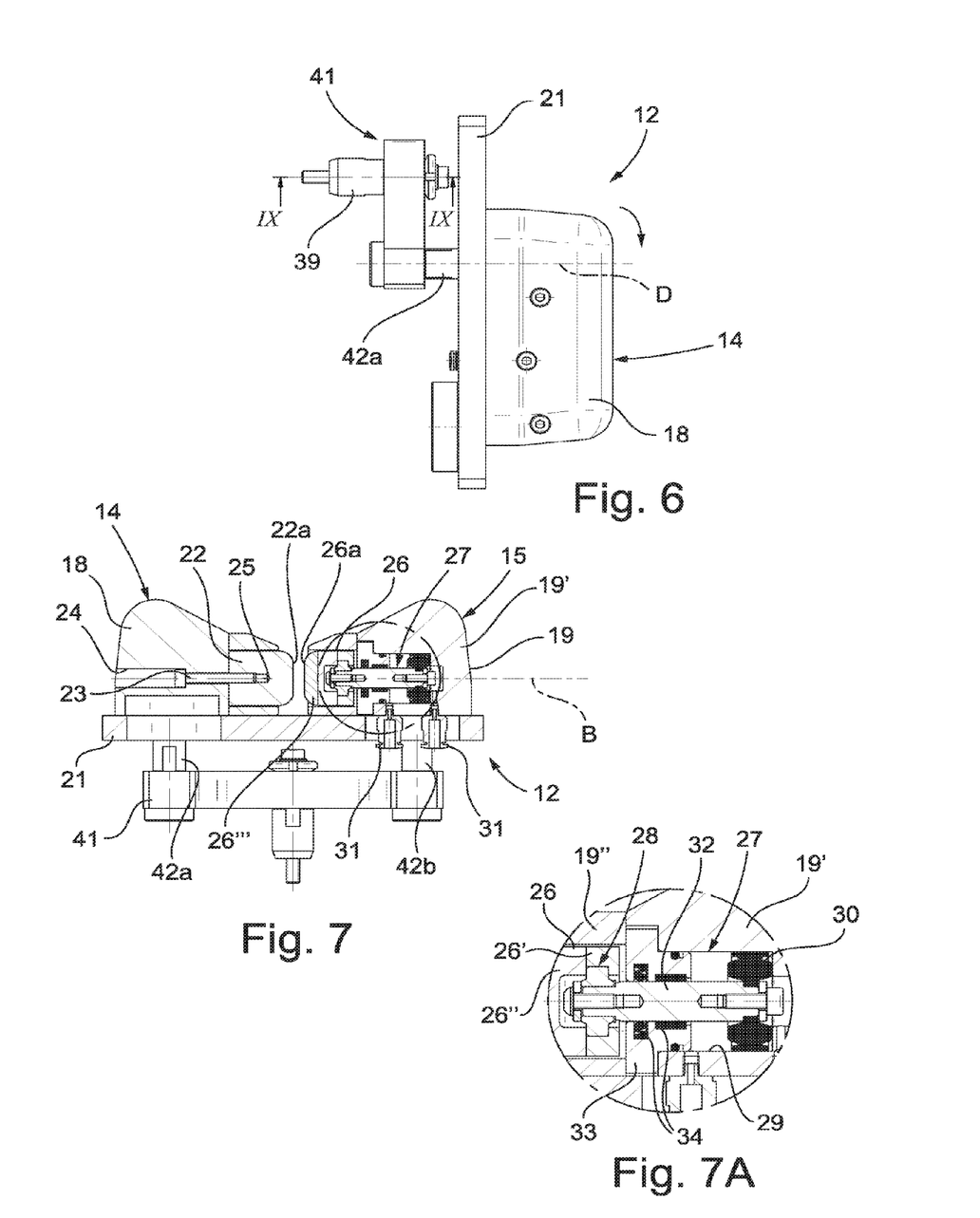
FIG. 7 is a section of FIG. 4 according to the plane VII-VII.
FIG. 7A shows a detail of FIG. 7 on an enlarged scale.
Figure 8:
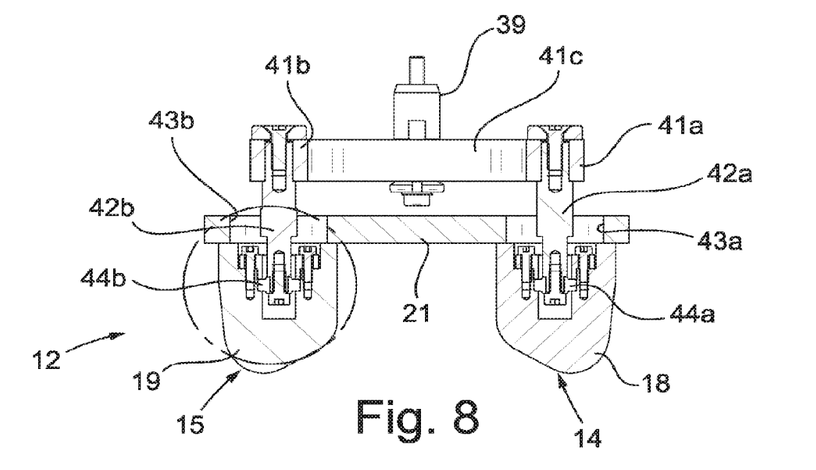
FIG. 8 is a section of FIG. 5 according to the plane VIII-VIII.
Figure 8A:
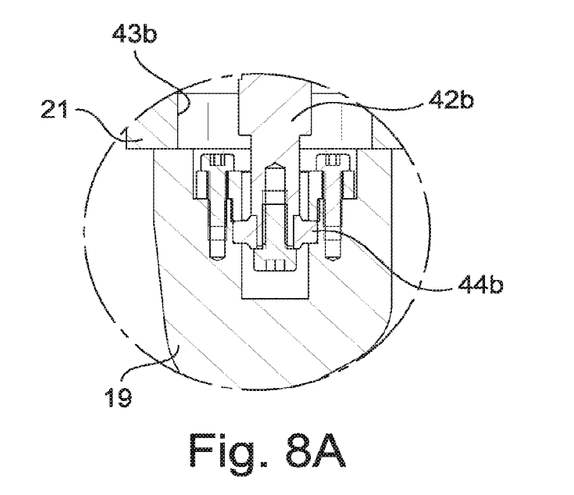
FIG. 8A shows a detail of FIG. 8 on an enlarged scale.
Figure 9:
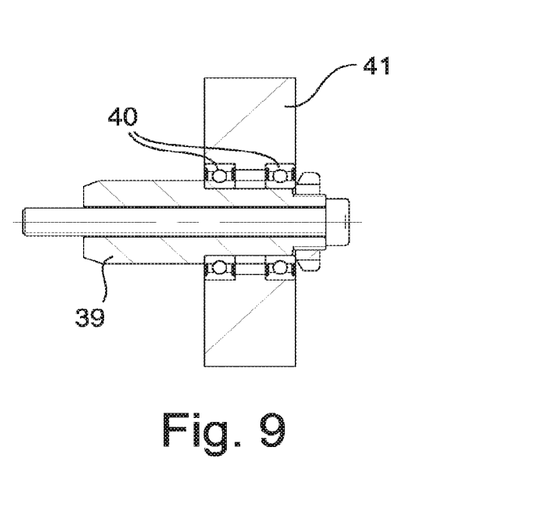
FIG. 9 is a section of FIG. 6 according to the plane IX-IX.
Figure 10:
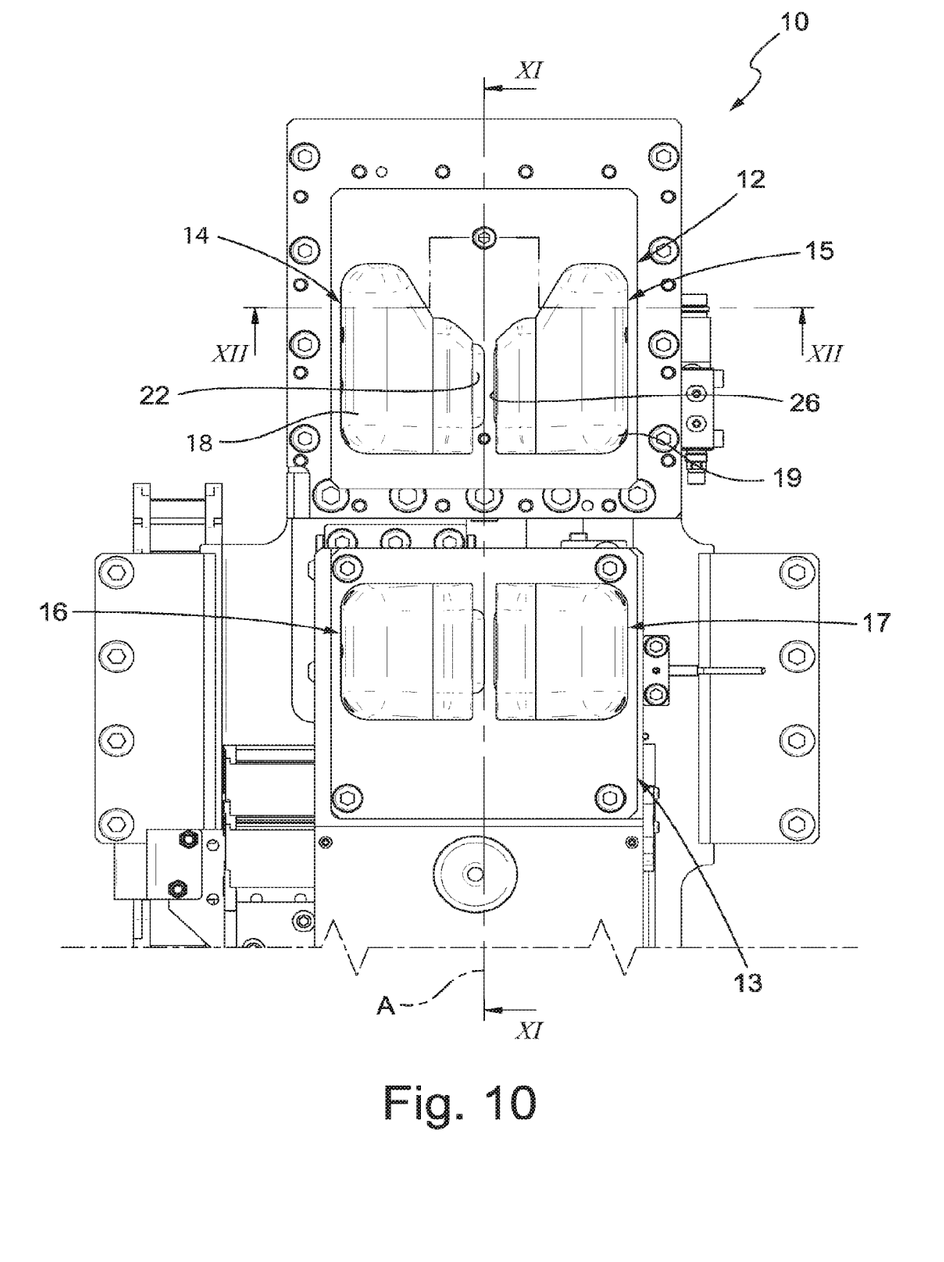
FIG. 10 is a front elevation view of a detail of the device according to the present invention comprising the first and the second clamps.

With reference to FIGS. 7 and 7A, the base body 19 comprises a first element 19' and a second element 19" fixed to one another; the cylindrical seat that defines the cylinder 29 is obtained in the first element 19', said seat having a blind bottom at one end that defines one of the two bases of the cylinder 29 and being closed at the opposite end by a cap 33 that is clamped between the first element 19' and the second element 19" and that defines the other base of the cylinder 29.

The piston 30 is mounted inside the cylinder 29, said piston 30, in practice, consisting of a gasket. The piston 30 is fixed to an end of the stem 32. The stem 32 is supported in a sliding manner along the second translation direction B by the cap 33 with interposition of sealing gaskets 34.

The end of the stem 32 opposite the piston 30 projects from the cap 33 towards the fixed jaw 14 and the clamping body 26 is mounted to it by means of the spherical joint 28. The clamping body 26 is made of more elements fixed to one another: a first support element 26' that is articulated to the stem 32 by means of the spherical joint 28, a second cap element 26" and a third "pad" element 26''' that defines the clamping surface 26a. The clamping body 26 is guided in a sliding manner in a corresponding seat obtained in the base body 19 and, in particular, in the second element 19" thereof.

As already indicated above, limited to such a first aspect of the present invention, the structure of the fixed jaw 16 and of the movable jaw 17 of the second clamp 13 is analogous to that described above with reference to the first clamp 12.

As it can easily be understood by the person skilled in the art, the pair of clamps is of the interchangeable type as a function of different types of textile samples.

According to a second aspect of the present invention, the first clamp 12 is coupled to the first detection means 47 for detecting the force so as to be able to carry out oscillations at least about a first axis C and, preferably, also about a second axis D different from the first axis C, so as to make the measurement of the force detected as independent as possible from pre-loads and friction and from the more or less centered position of the textile sample with respect to the jaws of the two clamps. As it will become clearer from the following description, the first clamp 12 is coupled to the first detection means 47 with a shaped coupling so as to eliminate hyperstaticity.

The first axis C is advantageously substantially orthogonal to a plane parallel both to the first traction direction A and to the second traction direction B; with reference to the attached figures, the first axis C is substantially horizontal and parallel to the axis X, i.e. substantially orthogonal to the vertical plane ZY.

The second axis D, on the other hand, is parallel to the second translation direction B (axis Y).

In greater detail (FIGS. 11 and 12), the first detection means 47 (i.e. sensors or transducers) comprise an elongated body 35 (in practice formed by a rod) that is arranged along a direction orthogonal to the plane ZY parallel to the first translation direction A and to the second translation direction B and that is supported in a box-shaped body 36 fixed to the housing 11 or in any case to the support frame of the device 10 by means of at least one loading cell 37 and, advantageously, by two loading cells 37, 38. The two loading cells 37 and 38 support the opposite ends of the elongated body 35 and are advantageously of the "S"-shaped type.

Figure 11:
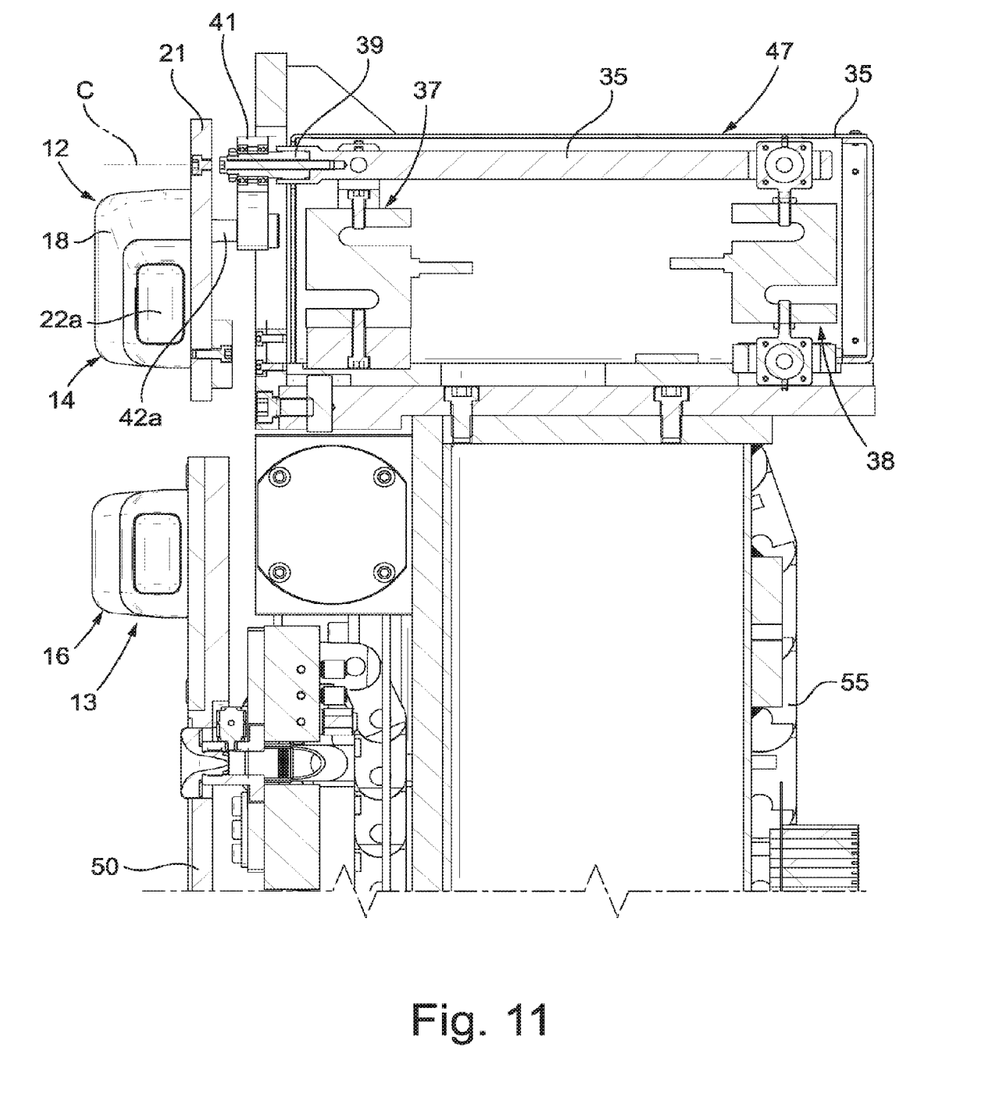
FIGS. 11 and 12 are sections of FIG. 10 according to the planes XI-XI and XII-XII, respectively.
Figure 12:
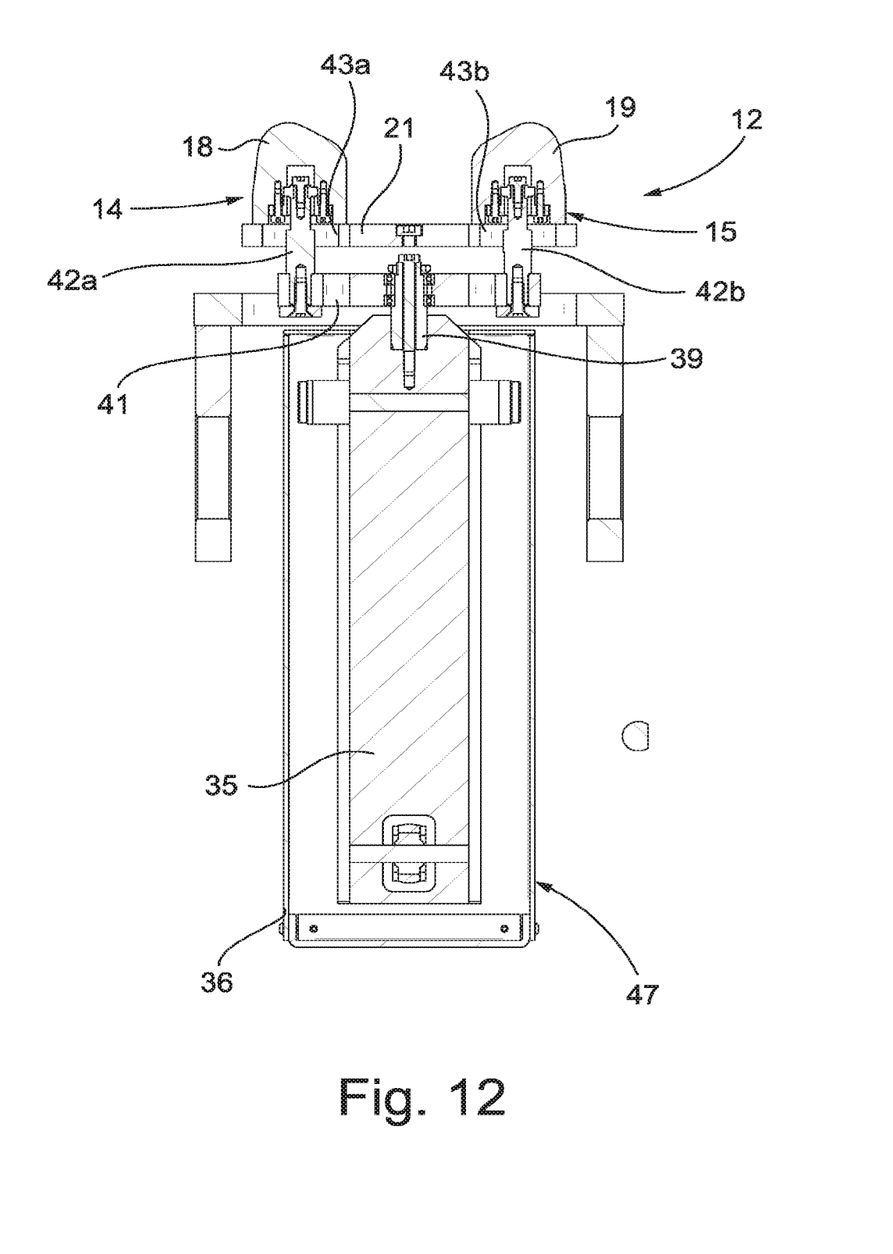

The first clamp 12 is coupled to an end of the elongated body 35 so as to be able to carry out oscillations both about the first axis C and about the second axis D. The first axis C is parallel or coaxial to the elongated body 35.

With reference to the embodiment represented in the attached figures, the plate 21 is supported in a rotating manner, by means of bearings 40, about a first pin 39 that is fixed to an end of the elongated body 35 and that is substantially coaxial to the elongated body 35. The first pin 39 defines the first axis C.

In particular, the plate 21 is mounted on a support bracket 41 that is articulated in a rotating manner about the first pin 39 by means of bearings 40; the support bracket 41 is arranged at the rear face of the plate 21, i.e. at the face of the plate 21 opposite the one at which the fixed jaw 14 and the movable jaw 15 are mounted.

The plate 21 is mounted on the support bracket 41 so as to be able to carry out oscillations about the second axis D.

For this purpose, the bracket 41 comprises two arms 41a and 41b that extend symmetrically from the central portion 41c thereof that is articulated to the first pin 39.

Each of the two arms 41a and 41b supports a respective second pin 42a and 42b that extends parallel to the first pin 39 and that inserts with clearance into a corresponding slot 43a and 43b obtained passing through the plate 21.

The two second pins 42a and 42b project with an end thereof from the front face of the plate 21. The ends of the two second pins 42a and 42b that project from the front face of the plate 21 are coupled by means of a respective spherical joint 44a and 44b respectively to the base body 18 of the fixed jaw 14 and to the base body 19 of the movable jaw 15.

A counter-weight 45 is fixed to the plate 21 at the side thereof opposite the one that, by means of the support bracket 41, is articulated to the first pin 39; the counter-weight 45 is vertically aligned to the first pin 39.

In a possible alternative embodiment not represented in the attached figures, the plate 21 is coupled to the first detection means 47 and, in particular, to the elongated body 35 thereof by means of a spherical joint.

According to a further aspect of the present invention, the movement means 46 comprise a belt 49 closed on itself as a loop and wound around a driving pulley and an idle pulley and to a portion of which a slide 50 is fixed, said slide 50 supporting the second clamp 13. In greater detail and with reference to FIGS. 13 and 14, the belt 49 is closed on itself as a loop and is wound around a pair of pulleys, the sole supports of which are shown: a first support 51 that supports the driving pulley by means of an electric gear motor 52 and a second support 53 that supports the idle pulley.

Figure 13:
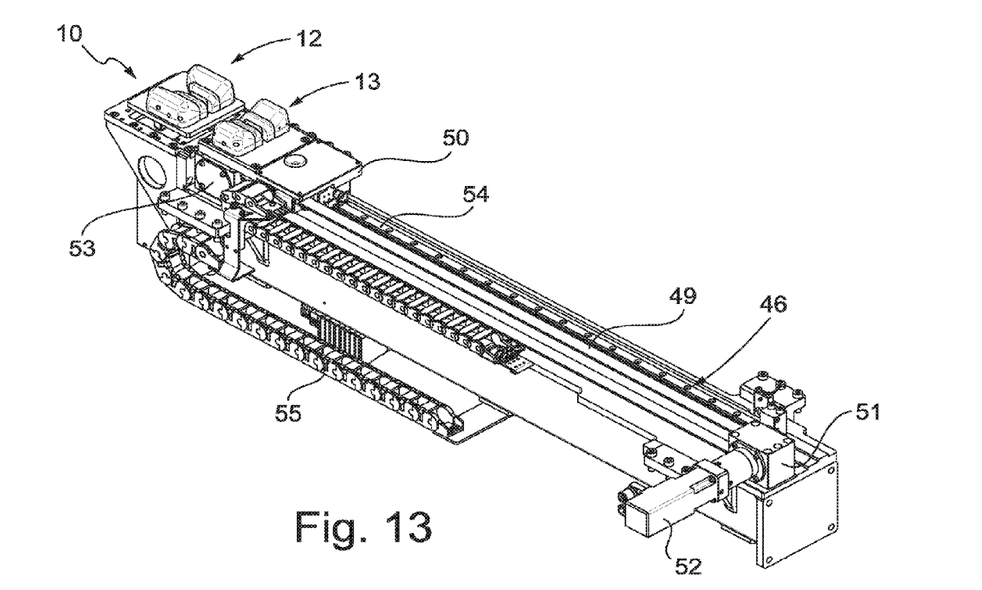
FIGS. 13 and 14 are two axonometric views of a detail of the device according to the present invention relative to the movement means and of the second detection means for detecting the position of the second clamp.
Figure 14:
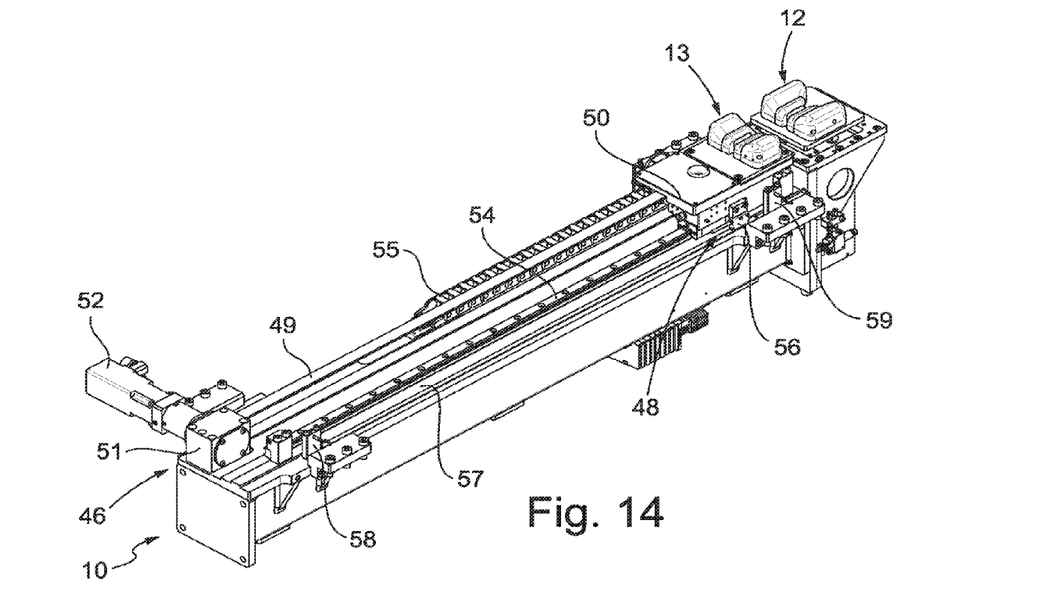

The slide 50 is fixed to a portion of the branch of the belt 49, on which slide 50 the second clamp 13 is mounted. The slide 50 is mounted in a sliding manner along a rectilinear guide 54 advantageously of the ball-recirculating type. A return chain 55 accompanies the sliding of the slide 50.

The second detection means 48 for detecting the position of the second clamp 13 comprise a position transducer 56 fixed to the slide 50. Advantageously, the position transducer or sensor 56 is of the magnetic type and cooperates with a magnetic band 57 fixed to a side of the rectilinear guide 54. There are also two end-stroke transducers 58 and 59 for the sliding of the slide 50.

The device 10 is complete with structural and functional modules, like for example those arranged to move the movable jaws, and to control and automatically manage the operation of entire device 10, which are not illustrated and described in detail since they are of the type that can be immediately understood by the person skilled in the art.

Figure 1:
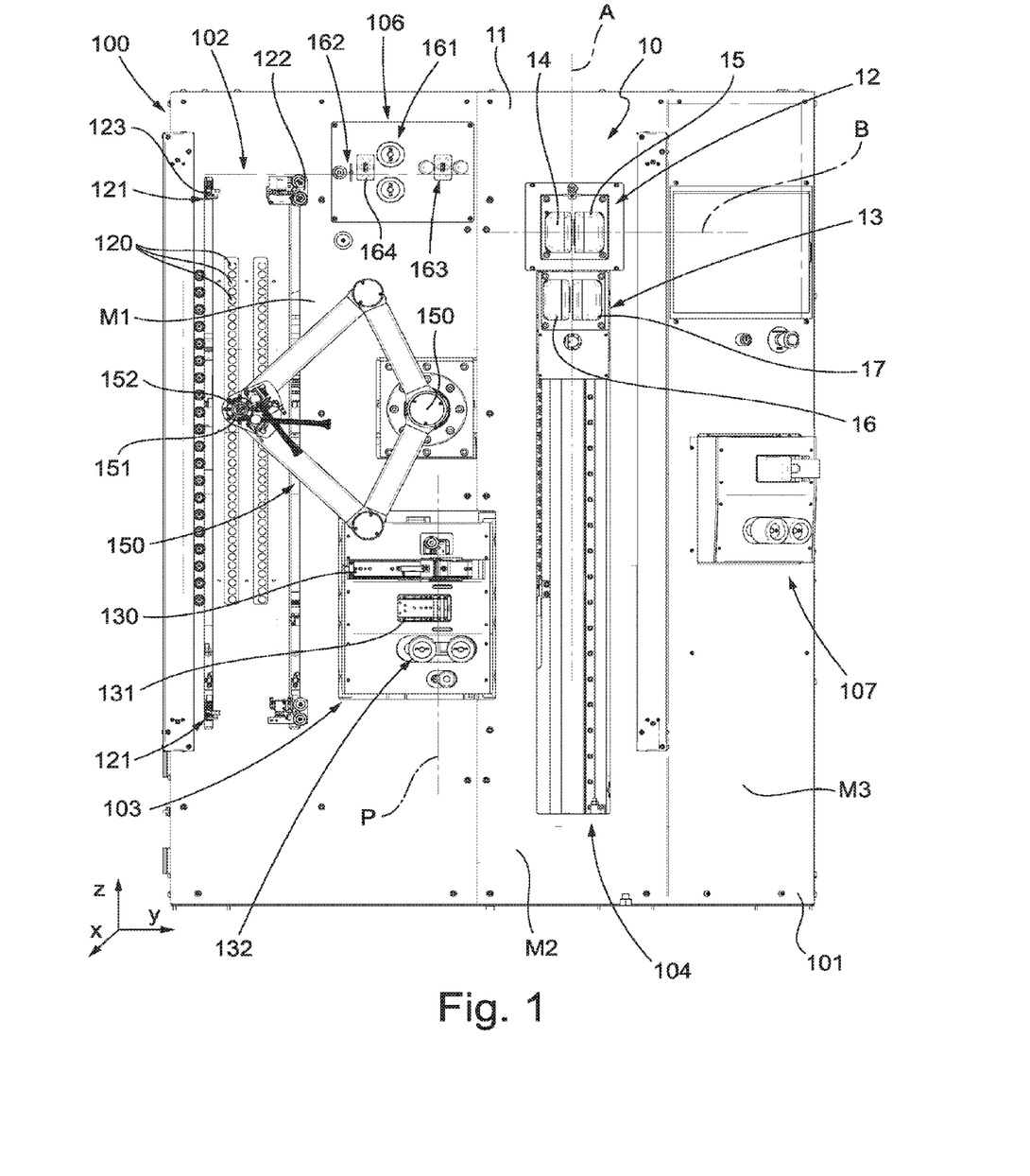
FIG. 1 is a front elevation view of a device according to the present invention applied to a modular automatic equipment for determining a plurality of features of textile samples.
Figure 2:
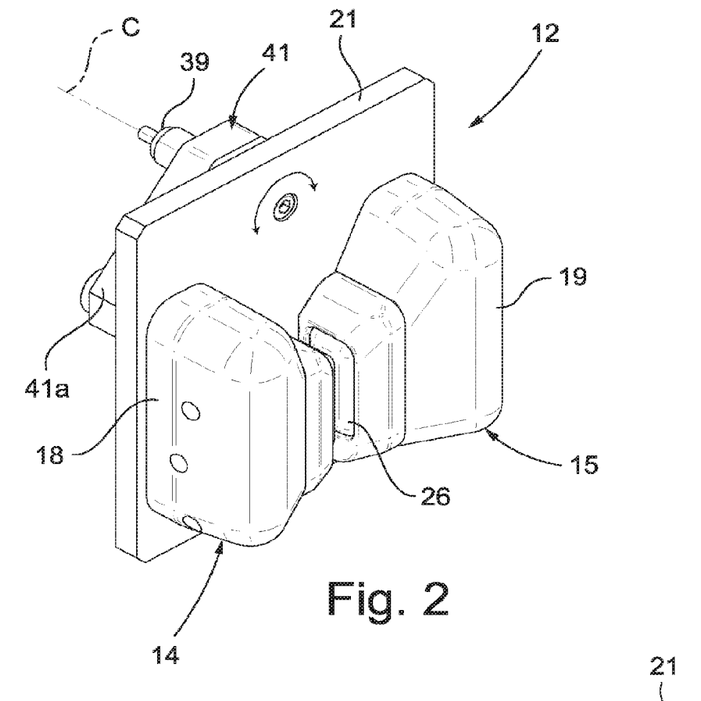
FIGS. 2 and 3 are axonometric views, from the front and rear side respectively, of the first clamp of the device according to the present invention.
Figure 3:
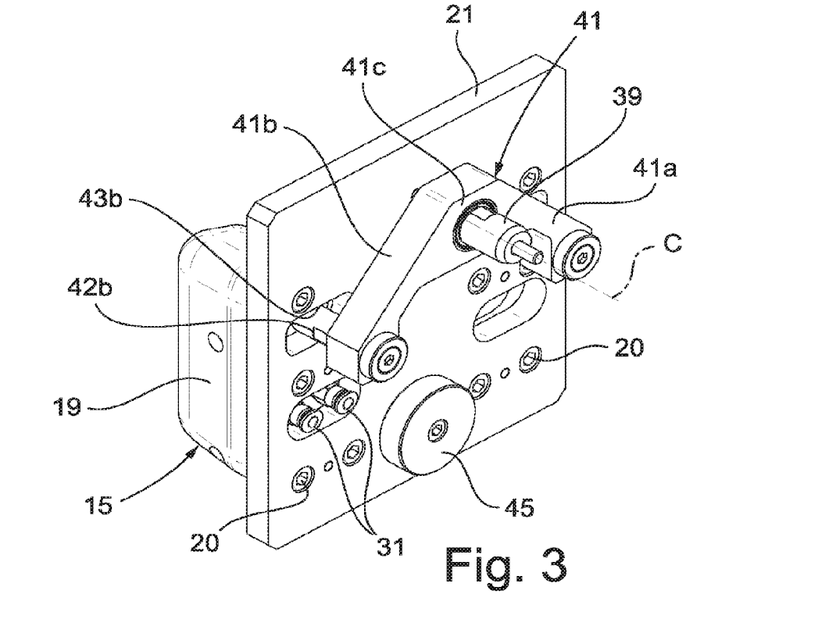
Figure 4:
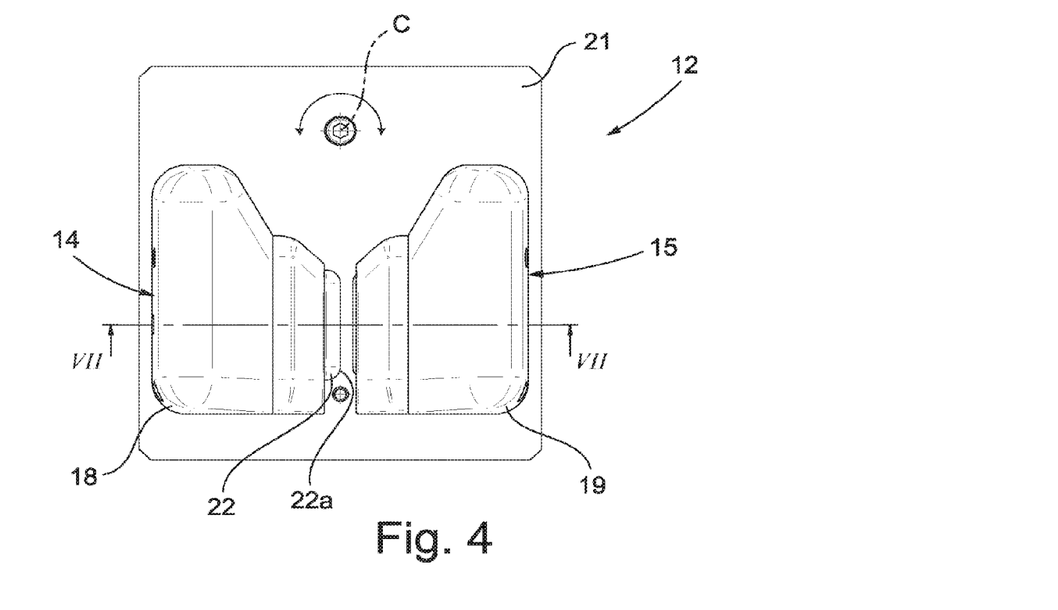
FIGS. 4, 5 and 6 show the first clamp of the device according to the present invention in a front elevation view, in a rear elevation view and in a side elevation view, respectively.
Figure 5:
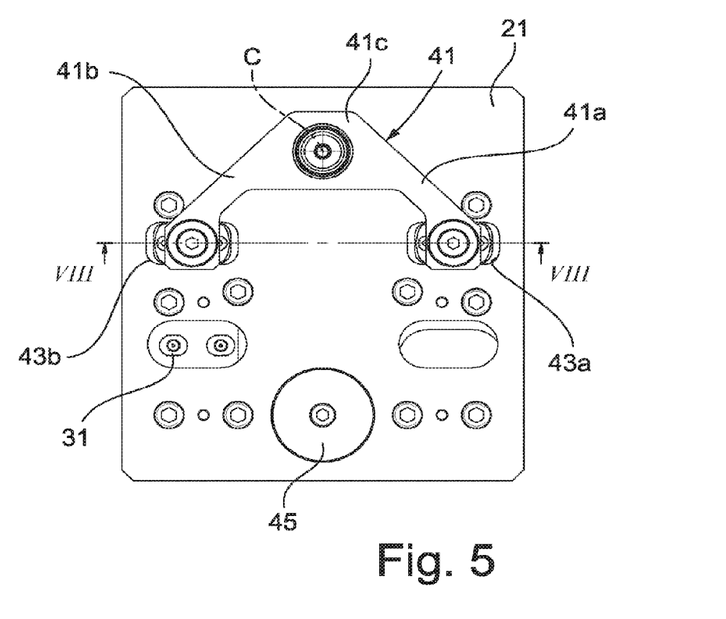

FIG. 1 shows the device 10 integrated as measurement module in an equipment 100 of the modular type for automatically carrying out quality control tests of elongated textile samples of the yarns, threads, tapes type and the like.

The equipment 100 is subject-matter of a simultaneous patent application to the same applicant and that is entirely referred to.

The equipment 100 comprises a housing 101 with which the following are associated:

a loading module 102 for loading the ends of a plurality of textile samples to be tested, each of which is wound in a corresponding feeding package (spindle, reel, spool or similar) supported by a creel associable with the equipment 100 and not shown, at least one first measurement module 103 for measuring at least one first structural feature of the textile samples, at least one second measurement module 104 for measuring at least one second physical-mechanical feature of the textile samples, handling means 105 adapted to handle the textile samples between the loading module 102, the first measurement module 103 and the second measurement module 104, a central unit of the programmable type (not shown) for managing and controlling the loading module 102, the at least one first measurement module 103, the at least one second measurement module 104 and the handling means 105 and for processing the measurements carried out by the at least one first measurement module 103 and by the at least one second measurement module 104, wherein the at least one first measurement module 103 and the at least one second measurement module 104 are adapted to operate successively or simultaneously on a same or on two different textile samples.

The equipment 100 can also comprise at least one third measurement module 106 for measuring a further structural feature of the textile samples and/or a fourth measurement module 107 for measuring a feature of textile samples of the tape or roves type manually insertable into it.

The first measurement module 103 is adapted to measure at least one structural feature of the textile samples selected from the evenness of the linear mass (count) and hairiness, advantageously both. The first measurement module 103, therefore, comprises a device for measuring hairiness 130 and a device for measuring evenness (evenness of the linear mass) 131, which are arranged one on top of the other and substantially aligned with each other or in any case alignable along a sliding path P of the textile sample and pulling means 132 aligned or in any case alignable with the path P and that are arranged below the device for measuring the hairiness 130 and the device for measuring the evenness 131 and that are configured to make the textile sample slide along the path P.

The second measurement module 104 is adapted to measure at least one physical-mechanical feature of the textile samples and, in particular, a dynamometric feature such as the elongation at break by tension, the tensile strength (i.e. the maximum stress under tension before breaking), the elastic modulus, the toughness and, in the embodiment represented in FIG. 1, it consists of a measurement device 10 according to the present invention.

The third measurement module 106 is adapted to measure a physical feature such as the linear mass (count) of the textile samples. The third measurement module 106 thus consists of a so-called count calculator.

The first measurement module 103 and the possible third and fourth measurement modules 106 and 107 are not described in detail since they are of the type known to the person skilled in the art.

In totally general terms, the first measurement module 103 comprises a device for measuring the hairiness 130 as for example described in IT1413638 patent application and a device for measuring the evenness 131 for example of the capacitive type.

In order to align the inlet opening of the device for measuring the hairiness 130 with that of the device for measuring the evenness 131, the former is supported by a slide that is movable on command along a horizontal direction orthogonal to the path P.

The pulling means 132 comprise a pair of rollers that can rotate in opposite senses and at controlled speeds and between which the textile sample being tested is pulled. These same pulling means 132 are supported by a respective slide that is movable on command along a horizontal direction orthogonal to the path P so as to be alignable with the inlet opening of the device for measuring the hairiness 130 and to keep the path P substantially rectilinear.

The third measurement module 106 comprises, in general terms, own means 161 for pulling the textile sample analogous to the pulling means 132, cutting means 162 for cutting a portion of the textile sample the length of which is determined indirectly from measurements of the movement of the pulling means 161, braking means 163 of the textile sample, suction means 164 for sucking the cut portion of sample and weighing means housed inside the housing 101. The fourth measurement module 107 is of the known capacitive evenness meter type.

The third measurement module 106 and the first measurement module 103 are aligned one above the other in a first measuring area M1.

The second measurement module 104 (i.e. the device 10) is arranged in a second measuring area M2 distinct from the first measuring area M1. The possible fourth measurement module 107 is arranged in a third measuring area M3 different from the first and from the second measuring area M1 and M2 and not reached by the handling means 105. It is specified that the fourth measurement module 107 can operate simultaneously and in parallel to the first measurement module 103 and to the second measurement module 104.

The handling means 105 are movable between the loading module 102, the first measuring area M1 and the second measuring area M2; they are made to carry out translation and/or rotation movements about the three axes XYZ.

In the represented embodiment, the handling means 105 comprise an articulated quadrilateral structure movable in the plane ZY and that has a cylindrical joint 150 coupled with actuator means not visible and a cylindrical joint 151 opposite the first and provided with a handling head 152 rotatable about the axis X and provided with gripper means for gripping and releasing the textile samples.

The handling means 105 are not described any further since they are of the type that can be immediately understood by the person skilled in the art.

The loading module 102 comprises a plurality of gripping members of the gripper member type 120 for locking the inlet ends of a corresponding plurality of textile samples to be tested each of which is wound in a corresponding package supported by a creel that is not shown.

The gripper members 120 are aligned along a loading direction that is advantageously vertical (i.e. parallel to the axis Z) and are individually movable between a locking position and an unlocking position for locking/unlocking the inlet end of a respective textile sample.

The loading module 102, moreover, comprises one or more, advantageously two, carriages 121, each of which is individually movable in translation in both senses along a direction parallel to the loading direction that they can selectively align with one of the gripper members 120.

Each carriage 121 is provided with at least one first support body 122 that is arranged at the side of the gripper members 120 facing towards the measurement modules and that supports at least one operating group selected from a cutting group, a braking group, a suction group and a guiding-return group of a textile sample. Each carriage 121, moreover, is advantageously provided with a second support body 123 that is arranged at the side of the gripper members 120 facing towards the supply (creel) of the textile samples and that supports at least one operating group selected from a braking group and a guiding-return group of the textile sample. Each carriage 121 is also provided with actuator means for actuating the gripper members between their locking position and their unlocking position.

Each carriage 121 is provided with its own motor means and is connected to the central control and management unit.

Each module of the equipment 100 is equipped with its own microprocessor connected to the central control and management unit, which makes the equipment 100 of the modular type and assemblable according to different needs.

The equipment 100 is not described and illustrated any further here.

It is specified that the configuration of the jaws of the first clamp and/or of the second clamp as described above and as represented in the attached figures and, in particular, the "oscillating" coupling of the clamping body of at least one of the fixed jaw and the movable jaw of at least one of the two clamps, can also be adopted in devices in which the fixed clamp is coupled to the first detection means for detecting the tensile force through different coupling means from those described above and as represented in the attached figures and vice-versa.

These two aspects of the present invention, although operating synergically for the purposes of obtaining precise measurements independent from the position of the thread and/or from possible friction, can also be adopted individually. Thus, for example, the first clamp or fixed clamp can be coupled to the first detection means for detecting the tensile force so as to oscillate about two different oscillation axes, irrespective of how the fixed and movable jaws thereof are made and, in particular, irrespective of how the clamping body of the movable jaw thereof is made.

Similarly, the configuration of the movement means of the second clamp or movable clamp and of the second detection means for detecting its position as described above and as represented in the attached figures can be adopted independently from the configuration of the first clamp and of the second clamp or from how the first clamp (fixed) is coupled to the first detection means for detecting the tensile force.

The device object of the present invention has the advantage of allowing the textile sample to be tested to be stably clamped, limiting sliding thereof with respect to the jaws of the two clamps. In particular, the possibility of oscillation of the clamping body of one or both of the jaws of one or both of the clamps allows the respective clamping surface to adapt and rest on the facing clamping surface of the corresponding counter-jaw so as to be able to stably clamp a portion of textile sample being tested against it, irrespective of the position of the textile sample.

The device object of the present invention also has the advantage of allowing precise detection of the tensile force applied to the textile sample being tested, eliminating possible force components due to undesired and indeterminable pre-loads and friction and irrespective of the position of the textile sample with respect to the two clamps. The device object of the present invention, thanks to the oscillating coupling of the first clamp (fixed) with the respective detection means for detecting the tensile force allows eliminating hyperstaticity that would affect the measurements of tensile force.

The device object of the present invention also has the advantage of allowing the movable clamp to be moved in a simple and accurate manner with relatively inexpensive mechanical means.

The device object of the present invention also has the advantage of allowing the position of the movable clamp to be detected directly and precisely.

The measurement device for measuring dynamometric features of elongated textile samples of the yarns, threads, tapes type and the like thus conceived can undergo numerous modifications and variants, all of which are covered by the invention; moreover, all of the details can be replaced by technically equivalent elements. In practice, the materials used, as well as the sizes, can be whatever according to the technical needs.

The invention claimed is:

1. A measuring device for measuring dynamometric features of elongated textile samples of the yarns, threads, tapes type and the like, said device comprising:
   a first clamp,
   a second clamp that is substantially aligned and relatively movable with respect to said first clamp along a first translation direction (A),
   wherein each of said first clamp and of said second clamp includes a fixed jaw and a movable jaw in relation to the respective said fixed jaw along a second translation direction (B) substantially orthogonal to said first translation direction (A), wherein said movable jaw is movable between a resting position, in which the movable jaw is spaced apart with respect to said respective fixed jaw, and an operating position, in which the movable jaw is near to said respective fixed jaw in order to clamp a respective portion of an elongated textile sample,
   first force detection means that are coupled to said first clamp for detecting the tensile force applied to said textile sample, and
   second movement detection means for detecting the relative movement of said second clamp with respect to said first clamp,
   wherein at least one of said fixed jaw and of said movable jaw of at least one of said first clamp and of said second clamp comprises:
   a base body to which a clamping body is coupled, said clamping body being provided with a clamping surface that faces a corresponding surface of the other respective said fixed jaw or said movable jaw for clamping said respective portion of textile sample,
   wherein said clamping body is coupled to said base body to be able to oscillate about at least two axes different from one another.

2. The device according to claim 1, wherein said clamping body is coupled to said base body by means of a spherical joint.

3. The device according to claim 2, wherein said base body supports a stem that is parallel to said second translation direction (B) and that has an end coupled to said clamping body by means of said spherical joint.

4. The device according to claim 3, wherein said movable jaw of at least one of said first clamp and of said second clamp comprises said base body and said clamping body that is coupled to said stem by means of said spherical joint, wherein said stem is supported by said base body in a movable manner with translation movement along said second translation direction (B) and wherein a linear actuator is provided for actuating said stem moving along said second translation direction (B).

5. The device according to claim 4, wherein said linear actuator is of the cylinder and piston type, wherein said piston is movable with respect to said cylinder and is fixed to said stem.

6. The device according to claim 1, wherein said first clamp is coupled to said first force detection means to be able to perform oscillations at least about a first axis (C).

7. The device according to claim 6, wherein said first clamp is coupled to said first force detection means to be able to perform oscillations at least about a second axis (D) different from said first axis (C).

8. The device according to claim 6, wherein said first axis (C) is substantially orthogonal to a plane parallel to said first translation direction (A) and to said second translation direction (B).

9. The device according to claim 7, wherein said second axis (D) is parallel to said second translation direction (B).

10. The device according to claim 6, wherein said first clamp is coupled to said first force detection means to be able to perform oscillations at least about a second axis (D) different from said first axis (C), wherein said first axis (C) is substantially orthogonal to a plane parallel to said first translation direction (A) and to said second translation direction (B) and said second axis (D) is parallel to said second translation direction (B).

11. The device according to claim 1, wherein said first force detection means comprise an elongated body that is arranged along a direction orthogonal to the plane parallel to said first translation direction (A) and to said second translation direction (B) and that is supported by at least one loading cell, wherein said first clamp is coupled to an end of said elongated body.

12. The device according to claim 11, wherein said elongated body is supported by at least two loading cells.

13. The device according to claim 11, wherein said first clamp is mounted on a plate that is rotatably supported about a first pin fixed to said end of said elongated body and substantially coaxial to said elongated body.

14. The device according to claim 13, wherein said plate is mounted on a support bracket to be able to perform oscillations about an axis parallel to said second translation direction (B), wherein said support bracket is rotatably coupled about said first pin.

15. The device according to claim 1, further comprising movement means for moving said second clamp sliding along said first translation direction (A), said movement means being of the belt type closed on itself as a loop and wound about a driving pulley and an idle pulley, wherein a slide, on which said second clamp is mounted, is fixed to a branch of said belt.

16. The device according to claim 15, wherein said second movement detection means comprise a position transducer that is mounted on said slide.

17. The device according to claim 1, wherein said first translation direction (A) is vertical, said second translation direction (B) is horizontal and said first clamp is arranged above said second clamp.

* * * * *